(12) United States Patent
Liu et al.

(10) Patent No.: US 9,765,293 B2
(45) Date of Patent: Sep. 19, 2017

(54) AGGLOMERATED MICROBIOLOGICAL MEDIA

(71) Applicant: 3M INNOVATIVE PROPERTIES COMPANY, St. Paul, MN (US)

(72) Inventors: Jie J. Liu, Woodbury, MN (US); Wensheng Xia, Woodbury, MN (US)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 0 days.

(21) Appl. No.: 14/415,744

(22) PCT Filed: Jul. 22, 2013

(86) PCT No.: PCT/US2013/051449
§ 371 (c)(1),
(2) Date: Jan. 20, 2015

(87) PCT Pub. No.: WO2014/018433
PCT Pub. Date: Jan. 30, 2014

(65) Prior Publication Data
US 2015/0191692 A1 Jul. 9, 2015

Related U.S. Application Data

(60) Provisional application No. 61/675,624, filed on Jul. 25, 2012.

(51) Int. Cl.
*C12N 1/20* (2006.01)
*C12N 1/14* (2006.01)
*C12N 1/16* (2006.01)

(52) U.S. Cl.
CPC ............... *C12N 1/20* (2013.01); *C12N 1/14* (2013.01); *C12N 1/16* (2013.01); *C12N 2500/46* (2013.01); *C12N 2500/60* (2013.01)

(58) Field of Classification Search
CPC ............... C12N 1/20; C12N 1/14; C12N 1/16
See application file for complete search history.

(56) References Cited

U.S. PATENT DOCUMENTS

| | | | |
|---|---|---|---|
| 3,202,731 A | 8/1965 | Grevenstuk et al. | |
| 4,071,412 A | 1/1978 | Eisenberg et al. | |
| 4,248,971 A | 2/1981 | Youssef | |
| 4,318,932 A | 3/1982 | Ewing et al. | |
| 4,565,783 A | 1/1986 | Hansen et al. | |
| 4,755,468 A | 7/1988 | Jung et al. | |
| 5,089,413 A | 2/1992 | Nelson et al. | |
| 5,137,812 A | 8/1992 | Matner | |
| 5,232,838 A | 8/1993 | Nelson et al. | |
| 5,364,766 A | 11/1994 | Mach et al. | |
| 5,424,122 A | 6/1995 | Crandall et al. | |
| 5,435,851 A | 7/1995 | Kasica et al. | |
| 5,462,860 A | 10/1995 | Mach | |
| 5,474,931 A | 12/1995 | DiSorbo et al. | |
| 5,601,998 A | 2/1997 | Mach et al. | |
| 5,741,538 A | 4/1998 | Stipp et al. | |
| 5,869,321 A | 2/1999 | Franklin | |
| 5,922,385 A | 7/1999 | Stipp et al. | |
| 6,383,810 B2 | 5/2002 | Fike et al. | |
| 6,406,729 B1 * | 6/2002 | Miller | A23C 9/16 426/285 |
| 7,977,044 B2 | 7/2011 | Rising et al. | |
| 2001/0018092 A1 | 8/2001 | Labergerie et al. | |
| 2008/0317842 A1 | 12/2008 | Bertelsen et al. | |
| 2011/0070335 A1 | 3/2011 | Brügger et al. | |

FOREIGN PATENT DOCUMENTS

| | | |
|---|---|---|
| EP | 0 398 703 | 11/1990 |
| EP | 1 166 645 | 1/2002 |
| EP | 2 123 164 | 11/2009 |
| JP | 59-42846 | 3/1984 |
| JP | 6-254382 | 9/1994 |
| WO | WO 01/39616 | 6/2001 |
| WO | WO 03/048313 | 6/2003 |

OTHER PUBLICATIONS

"The Art of Agglomeration", Powder Handling & Processing, vol. 11, No. 3, 1999; pp. 368.
Atlas, R., Handbook of Microbiological Media, 4th Edition; 2010; (Cover, copyright and table of contents consisting of 3 pgs).
Brochure entitled "Bēpex—Particle Processing Technology—Bepex/Schugi FLEX-O-MIX"; from BEPEX International LLC; 2 pgs. (date unknown but believed to be prior to the date of the filing of the present application).
Hemati, M. et al., "Fluidized bed coating and granulation: influence of process-related variables and physicochemical properties on the growth kinetics", Powder Technology, vol. 130; 2003, pp. 18-34.
Jinapong, N. et al., "Production of instant soymilk powders by ultrafiltration, spray drying and fluidized bed agglomeration", Journal of Food Engineering, vol. 84, 2008; pp. 194-205.
Srivastava, S. et al., "Fluid Bed Technology: Overview and Parameters for Process Selection", International Journal of Pharmaceutical Sciences and Drug Research, vol. 2, No. 4; 2010, pp. 236-246.

* cited by examiner

*Primary Examiner* — Teresa E Knight
(74) *Attorney, Agent, or Firm* — 3M Innovative Properties Company; Eric E. Silverman

(57) ABSTRACT

A method of making a flowable, dried agglomerated nutrient medium is provided. The method comprises introducing a nutrient component comprising a powdered nutrient, and an agglomeration liquid, into an agglomerator comprising a flow-through-type agglomeration chamber, wet-massing the nutrient component with the agglomeration liquid in the agglomeration chamber for a predetermined period of time to form agglomerated nutrient medium particles, and exposing the agglomerated nutrient medium particles to drying conditions for a period of time to form the dried, agglomerated nutrient medium. The nutrient component facilitates the growth of a microorganism. Compositions, articles, and kits comprising the flowable, dried agglomerated nutrient medium are also provided.

9 Claims, 1 Drawing Sheet

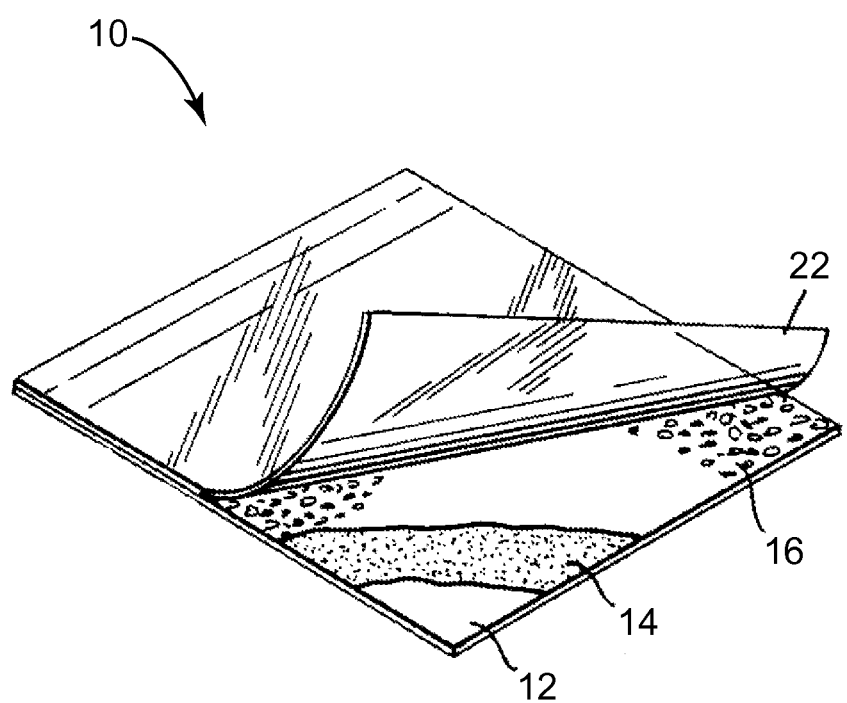

AGGLOMERATED MICROBIOLOGICAL MEDIA

CROSS REFERENCE TO RELATED APPLICATIONS

This application is a national stage filing under 35 U.S.C. 371 of PCT/US2013/051449, filed Jul. 22, 2013, which claims priority to U.S. Provisional Patent Application No. 61/675,624, filed Jul. 25, 2012, the disclosure of which is incorporated by reference in its entirety herein.

BACKGROUND

Nutrient media formulations have been used to cultivate a number of cell types including animal, plant and microbial cells. Cells cultivated in culture media catabolize available nutrients and produce useful biological substances such as monoclonal antibodies, hormones, growth factors, viruses and the like. Such products have therapeutic applications and, with the advent of recombinant DNA technology, cells can be engineered to produce large quantities of these products. Thus, the ability to cultivate cells in vitro is not only important for the study of cell physiology, but is also necessary for the production of useful substances which may not otherwise be obtained by cost-effective means.

Typical components of microbial culture media may include protein hydrolysates, inorganic salts, vitamins, trace metals, and carbohydrates, the types and amounts of which may vary depending upon the particular requirements of a given species of microorganism. Because these components tend to be more stable in a dehydrated form, they are frequently provided as dry, powdered formulations. The powdered formulations are added to water and, optionally, sterilized before use.

Culture media are typically produced in liquid form or in powdered form. Each of these forms has particular advantages and disadvantages.

For example, liquid culture medium has the advantage that it is provided ready-to-use (unless supplementation with nutrients or other components is necessary), and that the formulations have been optimized for particular cell types. Liquid media have the disadvantages, however, that they may require the addition of supplements (e.g., a vitamin or cofactor, and antibiotic) for optimal performance in cultivating a particular microorganism. Furthermore, most liquid media require some type of sterilization (e.g., autoclaving, filtration), which can be a time-consuming and/or expensive process.

To overcome some of the disadvantages, liquid culture medium can be made in concentrated form; the concentrate may be diluted to working concentrations prior to use. This approach provides the capability of making larger and variable batch sizes than with standard culture media, and the concentrated media formulations or components thereof often have longer shelf-life. U.S. Pat. No. 5,474,931 is directed to culture media concentrate technology and is incorporated herein by reference in its entirety. Despite these advantages, however, concentrated liquid media still have the disadvantages of their need for the addition of supplements, and may be difficult to sterilize economically.

As an alternative to liquid media, powdered culture media are often used. This approach has the advantages that larger batch sizes may be produced, the powdered media typically have longer shelf lives than liquid media, and the media can be sterilized by irradiation (e.g., gamma or ultraviolet irradiation) or ethylene oxide permeation after formulation. However, powdered media have several distinct disadvantages. For example, some of the components of powdered media become insoluble or aggregate upon lyophilization such that resolubilization is difficult or impossible. Furthermore, powdered media typically comprise fine dust particles which can make them particularly difficult to transfer and/or reconstitute without some loss of material, and which may further make them impractical for use in many biotechnology production facilities operating under GMP/GLP, USP or ISO 9000 settings.

Despite the advancements in rehydratable media, there still exists a need for rapidly dissolving nutritionally complex stable dry powder nutritive media, media supplements, media subgroups and buffers, which can be prepared in variable bulk quantities and which are amenable to sterilization.

SUMMARY

The present disclosure generally relates to nutrient media that are used to facilitate growth of a microorganism (e.g., a bacterium, a yeast, a mold). In particular, the present disclosure provides methods of agglomerating one or more powdered nutrient component to produce a dried, agglomerated nutrient medium. The methods include process conditions that provide agglomerated particles having a selected chemical composition, size, density, water content, or a combination of any two or more of the foregoing properties. In another aspect, the present disclosure further provides a composition comprising a dried agglomerated nutrient medium made according to any method disclosed herein. In another aspect, the present disclosure provides an articles and kits comprising any dried agglomerated nutrient composition disclosed herein.

Advantageously, the compositions of the present disclosure have a chemical composition that facilitates wetting of the surface of the particles by an aqueous solvent. Further advantageously, the compositions of the present disclosure have a density (e.g., a gravity-packed mean particle density) selected to facilitate submersion of the particles in an aqueous solvent. Even further advantageously, a dried agglomerated nutrient medium of the present disclosure has a particle size distribution selected to facilitate rapid dissolution of the particles in an aqueous solvent.

In one aspect, the present disclosure provides a method of making a flowable, dried agglomerated nutrient medium. The method can comprise introducing a nutrient component comprising a powdered nutrient, and an agglomeration liquid, into an agglomerator comprising a flow-through-type agglomeration chamber; wet-massing the nutrient component with the agglomeration liquid in the agglomeration chamber for a predetermined period of time to form agglomerated nutrient medium particles; and exposing the agglomerated nutrient medium particles to drying conditions for a period of time to form the dried, agglomerated nutrient medium. The nutrient component facilitates the growth of a microorganism. The agglomeration liquid is introduced as an atomized spray. In any embodiment of the method, the agglomeration liquid can consist of water. In any embodiment of the method, the agglomeration liquid can comprise a solvent having a dissolved nutrient that facilitates the growth of a microorganism. In any of the above embodiments of the method, introducing a nutrient component can comprise introducing a substantially uniform mixture of two or more powdered nutrients.

In any of the above embodiments of the method, the agglomerator further can comprise a mixing blade, wherein introducing a nutrient component into the agglomeration chamber comprises introducing the nutrient component at a feed rate of about 50 kg/hour to about 1000 kg/hour; wherein introducing an agglomeration liquid into the agglomeration chamber comprises introducing the agglomeration liquid at a spray rate of about 15 kg/hour to about 300 kg/hour; wherein the mixing blade is rotated at a blade rotation rate of about 500 rpm to about 4000 rpm; wherein exposing the agglomerated nutrient medium to drying conditions comprises exposing the agglomerated nutrient medium to a predetermined temperature of about 60° C. to about 85° C.; and wherein the feed rate, the spray rate, the blade rotation rate, and the predetermined temperature are selected to produce a dried agglomerated nutrient medium having a preselected mean water content of less than 5 weight percent. In any of the above embodiments of the method, the agglomerator further can comprise a mixing blade, wherein introducing a nutrient component into the agglomeration chamber comprises introducing the nutrient component at a feed rate of about 50 kg/hour to about 1000 kg/hour; wherein introducing an agglomeration liquid into the agglomeration chamber comprises introducing the agglomeration liquid at a spray rate of about 15 kg/hour to about 300 kg/hour; wherein the mixing blade is rotated at a blade rotation rate of about 500 rpm to about 4000 rpm; wherein exposing the agglomerated nutrient medium to drying conditions comprises exposing the agglomerated nutrient medium to a predetermined temperature of about 60° C. to about 85° C.; and wherein the feed rate, the spray rate, the blade rotation rate, and the predetermined temperature are selected to produce a dried agglomerated nutrient medium having a gravity-packed density of 0.2 to 0.5 grams per cubic centimeter. In any of the above embodiments of the method, the agglomerator further can comprise a mixing blade, wherein introducing a nutrient component into the agglomeration chamber comprises introducing the nutrient component at a feed rate of about 50 kg/hour to about 1000 kg/hour; wherein introducing an agglomeration liquid into the agglomeration chamber comprises introducing the agglomeration liquid at a spray rate of about 15 kg/hour to about 300 kg/hour; wherein the mixing blade is rotated at a blade rotation rate of about 500 rpm to about 4000 rpm; wherein exposing the agglomerated nutrient medium to drying conditions comprises exposing the agglomerated nutrient medium to a predetermined temperature of about 60° C. to about 85° C.; and wherein the feed rate, the spray rate, the blade rotation rate, and the predetermined temperature are selected to produce a dried agglomerated nutrient medium having particles of a first particle size distribution range of about 105 microns to about 2000 microns. In any of the above embodiments, the method further can comprise selecting a subpopulation of the particles, the subpopulation having a second particle size distribution range that is narrower than the first particle size distribution range, the second particle size distribution range being about 149 microns to about 1000 microns.

In any of the above embodiments of the method, one or more powdered nutrient can be selected from the group consisting of a protein, a carbohydrate, a salt and a mixture of any two or more of the foregoing powdered nutrients. In any of the above embodiments, the method further can comprise subjecting the dried agglomerated nutrient medium to a process that reduces the number of viable microorganisms in the dried agglomerated nutrient medium.

In another aspect, the present disclosure provides a composition comprising the flowable, dried agglomerated nutrient medium produced by the method of any one of the preceding claims. In any embodiment of the composition, a specified mass of the dried agglomerated nutrient medium can dissolve more rapidly than an equal mass of the nutrient component from which the agglomerated nutrient medium was made.

In yet another aspect, the present disclosure provides a kit comprising any of the above embodiments of the composition. In any embodiment of the kit, the composition can be disposed in a package comprising a predetermined mass of the dried agglomerated nutrient medium, wherein the predetermined mass can be mixed with 90 mL to 99 mL of aqueous diluent to produce a reconstituted medium capable of facilitating the growth of a microorganism. In any of the above embodiments, the kit further can comprise an article selected from the group consisting of a bag, a bottle, and a sample acquisition device. In any of the above embodiments, the kit further can comprise a selective agent and/or an indicator reagent.

In yet another aspect, the present disclosure provides a thin film culture device. The culture device can comprise a self-supporting waterproof substrate having first and second major surfaces; an adhesive layer disposed on at least a portion of the first major surface; a coating comprising the composition of any of the above embodiments disposed on a least a portion of the adhesive layer; and a dry, cold-water soluble gelling agent positioned for fluidic contact with the nutrient medium. In any of the above embodiments, the thin film culture device further can comprise a cover sheet coupled to a least a portion of the substrate, the cover sheet having a first side facing the first major surface.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

As used herein, "a," "an," "the," "at least one," and "one or more" are used interchangeably. Thus, for example, "a" particle can be interpreted to mean "one or more" particles.

The term "and/or" means one or all of the listed elements or a combination of any two or more of the listed elements.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

Additional details of these and other embodiments are set forth in the accompanying drawings and the description below. Other features, objects and advantages will become apparent from the description and drawings, and from the claims.

BRIEF DESCRIPTION OF DRAWINGS

FIG. 1 is a top perspective view, partially in section, of one embodiment of a thin film culture device according to the present disclosure.

DETAILED DESCRIPTION

Before any embodiments of the present disclosure are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. It is to be understood that other embodiments may be utilized and structural or logical changes may be made without departing from the scope of the present disclosure.

In general, the present disclosure relates to flowable, dried agglomerated particles made from water-soluble powders and a method of making said agglomerates. In some embodiments, the method can be used to make a nutrient medium for facilitating the growth of a microorganism. In contrast with at least one of the powders from which the agglomerated particles are made, and in contrast with other agglomerated particle compositions, a population of the inventive agglomerated particles advantageously possess two highly-desirable properties: 1) the agglomerated particles rapidly (i e, immediately or almost immediately) and substantially quantitatively sink below the surface of an aqueous liquid when poured onto the surface of the aqueous liquid and 2) the agglomerated particles rapidly dissolve into an aqueous liquid. Without being bound by theory, it is believed these highly-desirable properties result from the average size, surface area, surface composition, density and/or a unique combination of two or more of the foregoing physical attributes found in populations of agglomerated particles that are produced according to the present disclosure. Thus, in one aspect, the present disclosure provides a nutrient medium that rapidly disperses and dissolves into an aqueous liquid with little or no manual or mechanical agitation.

The present disclosure thus provides a method for the preparation of an agglomerated nutrient medium, the agglomerated medium being suitable to facilitate the recovery and/or growth of a microorganism, the method comprising i) introducing a nutrient component comprising a powdered nutrient and an agglomeration liquid into a flow-through-type agglomeration chamber (i.e., a "Schugi-type" agglomeration chamber), ii) wet-massing the nutrient component with the agglomeration liquid in the agglomeration chamber for a period of at the most 30 seconds to form an agglomerated nutrient medium, and iii) exposing the agglomerated nutrient medium to drying conditions for a period of time. According to the method of the present disclosure, the nutrient component (e.g., at least one powdered nutrient) facilitates the growth of a microorganism. Further, according to the method of the present disclosure, the agglomeration liquid is introduced as an atomized spray.

It has been found that a very short and intensive step of application of the agglomeration liquid and wet-massing of the composition comprising the nutrient leads to a population of agglomerated particles that is suitable for the preparation of a flowable dried nutrient medium.

The process time for the step of the application of the agglomeration liquid and wet-massing may vary depending on the equipment employed. In a specific embodiment, the wet-massing in step ii) is carried out in a time period of at the most about 20 sec such as, e.g., at the most about 15 sec, at the most about 10 sec or at the most about 5 sec.

An especially suitable apparatus for use in the present method is a vertical-path, flow-through-type agglomeration chamber manufactured by BEPEX International LLC. The model FX-100 Schugi FLEX-O-MIX mixer/agglomerator is preferred for the methods of the present disclosure, but the invention is not limited to the use of this particular model or manufacturer, other models and apparatus having a similar construction leading to a very fast step of wet-massing as mentioned above, are also within the scope of the present disclosure. In e.g. the Schugi FLEXOMIX, the wet-massing in step ii) is carried out in a time period of at the most about 1 sec preferably at the most about 0.5 sec, at the most about 0.4 sec, at the most about 0.3 sec or at the most about 0.2 sec.

A person having ordinary skill in the art will recognize, depending on the size of the apparatus employed, the feeding rate of the agglomeration chamber with the nutrient powder composition as well as the flow rate of the agglomeration liquid may vary.

Normally, in flow-through-type agglomeration apparatuses such as those used in according to the present disclosure, the agglomeration chamber is fed with the nutrient component (e.g. a powdered nutrient) using a feed rate from about 50 to about 1000 kg/h such as, e.g., from 50 to about 850 kg/h, from about 50 to about 750 kg/h, from 50 to about 500 kg/h, from about 50 to about 250 kg/h, from about 50 to about 200 kg/h, from about 100 to about 200 kg/h such as about 100 kg/h or about 200 kg/h.

In flow-through-type agglomeration equipment intended for very fast production, the agglomeration chamber is fed with a feeding rate of about 1000 to about 1500 kg/h such as, e.g., about 1100 to about 1300 kg/h.

The liquid flow of the agglomeration liquid is also an important parameter in a flow-through-type agglomeration chamber in order to obtain a fast and efficient step of application of the agglomeration liquid and wet-massing the composition. Normally, the agglomeration liquid is sprayed on the composition at a spray rate in a range of from about 15 to about 100 kg/h. Again, the flow rate depends on the size (e.g., chamber volume) of the equipment; larger equipment enables a higher flow rate than smaller equipment. In the exemplary apparatus described above (model FX-100 Schugi FLEX-O-MIX mixer/agglomerator), the agglomeration liquid can be sprayed on the composition at a spray rate in a range from about 15 to about 80 kg/h, inclusive; such as, e.g., from about 20 to about 60 kg/h, inclusive; from about 20 to about 50 kg/h, inclusive; from about 20 to about 40 kg/h, inclusive; or from about 25 to about 35 kg/h, inclusive. A person skilled in the art will know how to adjust the liquid flow depending on the equipment employed. As a guidance for larger equipment than that employed in the examples, the agglomeration liquid may be sprayed on the composition at a spray rate in a range from about 50 to about 300 kg/h, inclusive; such as, e.g., from about 60 to about 200 kg/h, inclusive; from about 65 to about 150 kg/h, inclusive; from about 70 to about 125 kg/h, inclusive; or from about 75 to about 105 kg/h, inclusive.

In any embodiment, the nutrient component and agglomeration liquid can be fed into the agglomeration chamber simultaneously and/or continuously. The continuous feeding of the powder composition as well as of the agglomeration liquid enables the process to be continuous, i.e. it may be continuously for a period of 1 day or more such as, e.g., 2 days or more, a 3 days or more, 4 days or more, 5 days or more or 7 days or more. In principle, the time period is determined based on the amount of dried agglomerated medium to be produced, but it may eventually be interrupted by clogging of parts of the apparatus that need to be rinsed.

In a specific embodiment using the Schugi FLEXOMIX equipment (or a similar apparatus) the nutrient component comprising the powdered nutrient (e.g., the powdered ingredients to make buffered peptone water) is fed through the top of the agglomeration chamber and passes through the chamber by means of gravity. The chamber contains a number of blades that enable an intensive wet-massing of the nutrient component. Compared with a high-shear mixing process, the step of application of the agglomeration liquid and the wet-massing according to the present method is much faster.

Nutrient Component

Methods of the present disclosure comprise a step of wet-massing a nutrient component with an agglomeration liquid. The nutrient component comprises at least one nutrient that facilitates the growth of a microorganism (e.g., a bacterium, a yeast, a mold). In any embodiment, the nutrient component may comprise a mixture of two or more nutrients that facilitate the growth of a microorganism. Non-limiting examples of suitable nutrients include a carbohydrate (e.g., a monosaccharide, a disaccharide, a trisaccharide, an oligosaccharide, or a polysaccharide), a protein, a protein hydrolysate, a cellular extract (e.g., yeast extract), a salt, a buffer component, a selective agent (e.g., an antibiotic), and a combination of any two or more of the foregoing nutrients.

In any embodiment, the nutrient component can be a substantially dry formulation (e.g., a substantially dry powder). Powdered media are typically produced by admixing the dried components of the culture medium via a mixing process, e.g., ball-milling, or by lyophilizing premade liquid culture medium. An exemplary nutrient medium that is used in the method of the present disclosure is buffered peptone water, which is commercially-available as a powder from a variety of sources including, for example, Oxoid Limited (Hampshire, UK) and Sigma-Aldrich (St. Louis, Mo.).

Other powdered nutrient media formulations that can be agglomerated according to the present disclosure include formulations that are rehydrated to produce buffered peptone water, trypticase soy broth, lactose broth, UVM modified Listeria enrichment broth, Buffered Listeria Enrichment broth (("BLEB"), Demi-Fraser broth, as well as other culture medium for microorganisms that are known in the art and may be found, for example in the Handbook of Microbiological Media (R. Atlas, ed., 4$^{th}$ Edition, 2010, CRC Press, Ann Arbor, Mich.), which is incorporated herein by reference in its entirety.

Agglomeration Liquid

An agglomeration liquid is sprayed into the agglomeration chamber to promote agglomeration of the smaller individual particles (e.g., powder particles) of the nutrient component into larger agglomerated particles. In any embodiment, the agglomeration liquid can comprise water (e.g., distilled and/or deionized water). In any embodiment, the agglomeration liquid can consist essentially of water (e.g., distilled and/or deionized water). In any embodiment, the agglomeration liquid can consist of water (e.g., distilled and/or deionized water). In any embodiment, the agglomeration liquid may comprise an organic solvent (e.g., ethanol, isopropanol).

Optionally, in any embodiment, a binder, especially a water-soluble binder, may be useful to facilitate the agglomeration of the nutrient component. The binder may be added (e.g., in the form of substantially dry particles such as a powder, for example) to the nutrient component or it may be dissolved or suspended in the agglomeration liquid.

Nonlimiting examples of suitable binders include biocompatible polymers (e.g. proteins, polyethylene glycol, polyvinylpyrollidone, polyvinyl alcohol, polysaccharides, dextrans, dextrins, maltodextrins, microcrystalline cellulose, hydroxypropylcellulose, hydroxypropyl cellulose, hydroxypropylmethylcellulose, methylcellulose, starch, and biocompatible derivatives of any of the foregoing polymers) and sugars (e.g., dextrose, fructose, glucose, inositol, erythritol, isomalt, lactitol, lactose, maltitol, maltose, mannitol, sorbitol, sucrose, tagatose, trehalose, and xylitol). In any embodiment, the binder may be a substance that facilitates the growth of a microorganism (e.g., a complete medium or diluent containing at least one nutrient). By way of example, a suitable agglomeration liquid for agglomerated buffered peptone water medium can be an solution of 1-50 weight percent buffered peptone water and a suitable agglomeration liquid for agglomerated trypticase soy broth medium cab be an aqueous solution of 1-50 weight percent trypticase soy medium.

The concentration of the binder in the composition comprising the nutrient may vary over a great range depending on the particular binder employed, but in general it is between from about 0.1% to about 40% w/w such as, e.g. from about 0.2 to about 35% w/w, from about 0.3 to about 30% w/w or from about 0.4 to about 25% w/w or from about 0.4 to about 24.2% w/w. In the case of sorbitol, the concentration is normally about 20-30% w/w and in the case of sugar alcohols other than sorbitol; the concentration is normally in the higher range such as from about 30 to about 40% w/w.

Preferably, the agglomeration liquid is an aqueous medium. In the case where the binder is included in the agglomeration liquid, the agglomeration liquid is prepared by dissolving the binder in water. Alternatively the binder can be admixed in a dry form to the powder.

The agglomerated nutrient medium is subjected to drying in a suitable drying chamber. It maybe a drying chamber that is operatively coupled to the agglomeration apparatus. The drying chamber may be operated batch wise or continuously and, optionally, may be segregated into two or more independently-controlled drying zones, the zones being operated at different temperatures.

In any embodiment, the agglomeration liquid may comprise a nutrient medium that facilitates the growth of a microorganism. For example, in one embodiment, the agglomeration liquid may comprise buffered peptone water broth (water, 10.0 g/L peptone, 5.0 g/L sodium chloride, 9.0 g/L disodium hydrogen orthophosphate 12H$_2$O, and 1.5 g/L potassium dihydrogen orthophosphate).

A method according to the present disclosure is used to make an agglomerated nutrient medium (e.g., a dried, wet-agglomerated nutrient medium). The agglomerated nutrient medium may be an agglomerated microbiological nutrient medium that facilitates the growth of a microorganism (e.g., a bacterium, a yeast, a mold). A method of the present disclosure comprises introducing a nutrient component comprising a powdered nutrient, and an agglomeration liquid, into an agglomeration chamber. The agglomeration chamber can be a component of a system that uses the Schugi mixing method (see, for example, "The Art of Agglomeration", 1999, Powder Handling & Processing, volume 11, page 368, which is incorporated herein by reference in its entirety) to produce agglomerated particles. An exemplary system is the vertical path Schugi FLEXOMIX FXD-100 mixer/agglomerator, available from Bepex International, LLC (Minneapolis, Minn.). The agglomeration chamber can have a first end, a second end opposite the first end and a mixing blade (e.g., a knife blade) disposed therebetween. The chamber may be configured with a substantially vertical path for the passage of materials from the first end of the chamber to the second end of the chamber.

In some embodiments, the mixing blade forms an angle with the shaft to which it is attached. The blade angle can be adjusted between 75° and 105° relative to the shaft. A person having ordinary skill in the art will recognize the blade angle can be adjusted to achieve optimal control of the particle size and particle size distribution of the agglomerated nutrient medium particles.

In any embodiment, the nutrient component and the agglomeration fluid can be introduced into the agglomeration chamber proximate the first end of the chamber. In any embodiment, the nutrient component can be fed (e.g., by gravity flow) into the agglomeration chamber via a powder dispenser. In any embodiment, the agglomeration fluid may be introduced into the chamber via one or more nozzle that forms an atomized spray (e.g., an air-driven atomized spray). The nutrient component can be any suitable nutrient component described herein. In any embodiment, the nutrient component can comprise a substantially uniform mixture of two or more powdered nutrients.

In any embodiment, a method of the present disclosure further comprises wet-massing the nutrient component with the agglomeration liquid in the agglomeration chamber for a predetermined period of time (e.g., at the most, about 30 seconds; at the most, about 20 seconds; at the most, about 10 seconds; at the most, about 5 seconds; at the most, about 1 second; preferably at the most, about 0.5 sec; at the most, about 0.4 seconds; at the most, about 0.3 seconds; or at the most, about 0.2 seconds) to form an agglomerated nutrient medium. In any embodiment, the predetermined period of time can be selected to result in agglomerated particles with a particular water content or a particular range of water contents. In any embodiment, a mixing blade (e.g., a rotating knife blade) can be used to facilitate contact between the nutrient component and the agglomerator fluid and/or to limit the size of the agglomerated nutrient medium particles.

In any embodiment, the method further comprises exposing the agglomerated nutrient medium particles to drying conditions for a period of time. In any embodiment, the agglomerated nutrient medium particles can be exposed to a gas (e.g., air), preferably at ambient temperature or higher, to cause drying of the particles. In any embodiment, the drying conditions (e.g., temperature, time, and gas or air flow) can be selected to produce agglomerated nutrient medium particles having a preselected average water content and/or a preselected range of water content. In any embodiment, the drying temperature can be about 60° C. to about 85° C., inclusive. In any embodiment, the drying temperature can be about 60° C. to about 65° C., inclusive. In any embodiment, the drying temperature can be about 65° C. to about 70° C., inclusive. In any embodiment, the drying temperature can be about 70° C. to about 75° C., inclusive. In any embodiment, the drying temperature can be about 75° C. to about 80° C., inclusive. In any embodiment, the drying temperature can be about 80° C. to about 85° C., inclusive.

In some embodiments, the mixing chamber may be operatively coupled to a dryer (e.g., a fluidized bed dryer) such that, after the agglomerated nutrient medium particles pass (e.g., by gravity flow) from the first end to the second end of the mixing chamber the particles move into a drying zone (e.g., the fluidized bed dryer). In these embodiments, the temperature, gas (e.g., air) flow, and residence time in the drying zone can be preselected to yield particles with a preselected water content. In any embodiments, the dryer may comprise a plurality of segregated drying zones, each zone having a particular temperature and residence time parameter for processing the particles. In any embodiment, the drier may comprise a cooling zone.

In any embodiment of the method, the agglomeration liquid may comprise at least one dissolved nutrient that facilitates the growth of a microorganism. In one embodiment, the agglomeration liquid comprises buffered peptone water.

A method according to the present disclosure comprises introducing a nutrient component into a agglomeration chamber. In any embodiment, introducing a nutrient component into the agglomeration chamber comprises introducing the nutrient component at a feed rate. A person having ordinary skill in the art will recognize the rates of introducing the nutrient component and the agglomeration liquid can affect the physical parameters (e.g., size, mass, density, and shape) of the agglomerated particles. Furthermore, the feed rate typically will vary according to the volume and geometry of the agglomeration chamber. Thus, in an embodiment of the method wherein the agglomeration process is conducted in a Schugi FLEXOMIX FX-100 agglomerator available from Hosokawa Micron (Summit, N.J.), the feed rate of the nutrient component can be from about 200 to about 1000 kg/h (e.g., from 300 to about 850 kg/h, from about 300 to about 750 kg/h, from 300 to about 700 kg/h, from about 350 to about 650 kg/h, from about 400 to about 600 kg/h, from about 450 to about 550 kg/h, such as about 500 kg/h.

A method according to the present disclosure comprises introducing an agglomeration liquid into a agglomeration chamber. In any embodiment, introducing an agglomeration liquid into the agglomeration chamber comprises introducing the agglomeration liquid at a spray rate. A person having ordinary skill in the art will recognize the rates of introducing the nutrient component and the agglomeration liquid can affect the physical parameters (e.g., size, mass, density, and shape) of the agglomerated particles. Furthermore, the spray rate typically will vary according to the volume and geometry of the agglomeration chamber and the feed rate and composition of the powder. Thus, in an embodiment of the method wherein the agglomeration process is conducted in a Schugi FLEXOMIX FX-100 agglomerator available from Hosokawa Micron (Summit, N.J.), the spray rate of the agglomeration liquid can be in a range from about 15 to about 80 kg/h, inclusive; such as, e.g., from about 20 to about 60 kg/h, inclusive; from about 20 to about 50 kg/h, inclusive; from about 20 to about 40 kg/h, inclusive; or from about 25 to about 35 kg/h, inclusive. A person skilled in the art will know how to adjust the liquid flow depending on the equipment employed. As a guidance for equipment that is larger than a Schugi FLEXOMIX FX-100 agglomerator, the agglomeration liquid may be sprayed into the agglomeration chamber at a spray rate in a range from about 50 to about 300 kg/h, inclusive (e.g., from about 60 to about 200 kg/h, inclusive; from about 65 to about 150 kg/h, inclusive; from about 70 to about 125 kg/h, inclusive; or from about 75 to about 105 kg/h, inclusive).

In any embodiment, the agglomerator used in a method of the present disclosure can comprise a mixing blade. The mixing blade may be coupled to a shaft. The mixing blade is rotated during the agglomeration process to accomplish one or more functions including, but not limited to i) to facilitate contact between the nutrient component and the agglomeration liquid, ii) to control the particle size of the agglomerated particles and/or iii) to facilitate the movement of particles through the agglomeration chamber. In any embodiment, the mixing blade can be rotated at about 500 rpm to about 5000 rpm, inclusively. In some embodiments, the mixing blade can be rotated at 3000 rpm. In some embodiments, the mixing blade can be rotated at 4000 rpm. A person having ordinary skill in the art will recognize the rotation rate and/or geometry of the mixing blade may be used to control the particle shape, effective particle size (e.g., average particle size and/or particle size range), density, and/or packed density of the agglomerated nutrient medium particles, as described above.

Thus, at least some of the process conditions (e.g., nutrient feed rate, agglomeration liquid spray rate, blade rotation rate, and/or predetermined drying temperature) can affect one or more of the physicochemical properties of the dried agglomerated nutrient medium particles produced by the method if the present disclosure. These properties include, but are not limited to the average effective particle diameter, the average particle diameter, the particle shape, the average particle mass, the average particle moisture content, the range of effective particle diameters, the range of particle masses, and/or the range of particle moisture content. One or a combination of any two or more of the physicochemical properties can affect the hydrodynamic properties (e.g., particle sink rate in an aqueous liquid, particle dissolution time in an aqueous liquid) of the dried, agglomerated nutrient medium particles.

In any embodiment, a method according to the present disclosure yields a population of dried, agglomerated nutrient medium particles having an average effective particle diameter and a first particle size distribution range. In any embodiment, the first particle size distribution range can comprise agglomerated particles having an effective particle diameter from about 105 microns to about 2000 microns. In any embodiment, the first particle size distribution range can comprise agglomerated particles having an effective particle diameter from about 105 microns to about 1000 microns.

In any embodiment, the method further can comprise isolating a subpopulation of the dried, agglomerated nutrient medium particles, the subpopulation having a preselected average effective particle diameter and/or having an effective particle diameter that falls within a second particle size distribution range. The subpopulation can be isolated using particle size-selection methods known in the art (e.g., using sieves that permit the retention or passage of particles with predetermined effective particle diameters. In any embodiment, the subpopulation may include agglomerated particles having an effective particle diameter from about 149 microns to about 1000 micron, inclusive. In any embodiment, the subpopulation may include agglomerated particles having an effective particle diameter from about 149 microns to about 850 microns, inclusive. In any embodiment, the subpopulation may include agglomerated particles having an effective particle diameter from about 149 microns to about 400 microns, inclusive. In any embodiment, the subpopulation may include agglomerated particles having an effective particle diameter from about 250 microns to about 400 microns, inclusive.

In any embodiment of the method, the dried agglomerated nutrient medium particles can have a preselected mean water content. A person having ordinary skill in the art will recognize the desired mean water content can be achieved by adjusting certain process parameters such as, for example, the spray rate, the drying temperature, and/or the drying time. The mean water content can be measured, for example, using the Karl Fischer titration method. In any embodiment, the mean weight percent water can be preselected to be less than about 5 weight percent water. In any embodiment, the mean weight percent water can be preselected to be less than or equal to about 3 weight percent water.

In any embodiment of the method, the dried agglomerated nutrient medium particles can have a gravity-packed density. The gravity-packed density of the dried, agglomerated nutrient medium particles can be measured, for example, by pouring a predefined volume (e.g., 100 mL) of the particles into a graduated cylinder, and measuring the mass of the particles in order to calculate the average density. The gravity-packed density can be from about 0.2 grams per cubic centimeter to about 0.5 grams per cubic centimeter.

In any of the above embodiments, a method of the present disclosure further can comprise subjecting the dried agglomerated nutrient medium to a process that reduces the number of viable microorganisms in the dried agglomerated nutrient medium. In any embodiment, the dried agglomerated nutrient medium can be treated with ethylene oxide vapor in order to reduce the number of viable microorganisms according to methods that are known in the art. After treatment with ethylene oxide vapor, the nutrient medium can be allowed to aerate before use, in order to reduce or eliminate residual ethylene oxide in the ethylene oxide-treated agglomerated medium. In any embodiment, the dried agglomerated nutrient medium can be treated with ionizing radiation (e.g., gamma radiation) or a source of ultraviolet light in order to reduce the number of viable microorganisms according to methods that are known in the art. The dried, agglomerated medium can be exposed to a source of gamma irradiation as described in U.S. Pat. No. 6,383,810, which is incorporated herein by reference in its entirety.

In addition to methods of making a flowable, dried agglomerated nutrient medium, the present disclosure further provides a composition of flowable, dried agglomerated nutrient medium prepared according to any of the embodiments of the method disclosed herein. The composition can be used to prepare nutrient medium to facilitate the recovery and/or growth of a microorganism in a sample (e.g., a clinical sample, an environmental sample, a food sample, a beverage sample, a water sample). Moreover, the composition can be used in an article for culturing microorganisms.

Advantageously, a composition of the present disclosure is flowable (e.g., can be poured from one container into another), is substantially free of dust (e.g., the smaller particles of nutrient from which the agglomerated medium is made and, when the agglomerated medium is made from a substantially dry starting material that includes at least one water-soluble powder, the agglomerated medium can dissolve in water substantially faster than the starting material. When the dissolution time is measured by pouring 2.55 g to 4.44 grams of a dried, agglomerated nutrient medium (e.g., a dried, agglomerated nutrient medium used to make buffered peptone water, trypticase soy broth, or modified Listeria recovery medium, for example) into a vessel containing 100 mL of deionized water and holding the vessel at room temperature without stirring, the dried agglomerated medium can dissolve in less than 5 minutes. In some embodiments, the dried agglomerated medium can dissolve in less than 4 minutes. In some embodiments, the dried agglomerated medium can dissolve in less than 3 minutes. In some embodiments, the dried agglomerated medium can dissolve in less than 2 minutes. In some embodiments, the dried agglomerated medium can dissolve in less than 1 minute.

Thus, in yet another aspect, the present disclosure provides an article for culturing a microorganism. A nonlimiting example of an article according to the present disclosure is a thin film culture device similar to the powder-coated devices described in U.S. Pat. Nos. 4,565,783 and 5,089,413; which are incorporated herein by reference in their entirety. The dried, agglomerated nutrient medium of the present disclosure can be used in place of the powdered nutrients in the thin film culture devices.

FIG. 1 shows one embodiment of a thin film culture device according to the present disclosure. The culture device 10 includes a body member comprising a self-supporting water-proof substrate 12 having upper and lower surfaces. Substrate 12 is preferably a relatively stiff film of a material such as polyester, polypropylene or polystyrene which will not absorb or otherwise be affected by water. Polyester films approximately 0.004 to 0.007 inch (0.1 to 0.18 mm) thick, polypropylene films approximately 0.004 to 0.008 inch (0.1 to 0.2 mm) thick and polystyrene films approximately 0.015 inch (0.38 mm) thick have been found to work well. Other suitable substrates include paper with a polyethylene or other water-proof coating. An example of a suitable polyethylene-coated paper substrate is "Schoeller Type MIL" photoprint paper (commercially available from Schoeller Pulaski, New York, N.Y.). The substrate 12 may be either transparent or opaque, depending on whether one wishes to view bacterial colonies through the substrate. To facilitate the counting of bacterial colonies, the substrate 12 preferably has a square grid pattern printed thereon as described in U.S. Pat. No. 4,565,783, for example.

Substrate 12 is coated on its upper surface with a layer of an adhesive 14 which serves to hold the dry gelling agent and/or nutrients in a uniform monolayer for easy hydration. Adhesive 14 should be water-insoluble and non-inhibitory to the growth of microorganisms. Preferably, the adhesive is sufficiently transparent when wet to enable the viewing of bacterial colonies through the film coated with the adhesive. It is preferred that adhesive 14 be pressure-sensitive. However, heat-activated adhesives wherein a lower melting substance is coated onto a higher melting substance may also be used. Water-activated adhesives such as mucilage may also be useful.

Adhesive 14 should be coated onto substrate 12 in a thickness which is preferably less than the diameter of the particles of the powdered gelling agent and/or nutrients. The object is to apply enough adhesive to adhere the particles to the substrate but not so much that the particles become completely embedded in the adhesive. A uniform monolayer of powder 16 is desired with sufficient surface area exposed for hydration. Generally, an adhesive layer in the thickness range of 0.0002 to 0.0005 inch is suitable. The powders, including the dried, agglomerated nutrient medium of the present disclosure, can be coated onto the adhesive layer as described in U.S. Pat. No. 4,565,783, for example.

Adhered to one edge of spacer 18 of the body member is an optional cover sheet 22. Cover sheet 22 is preferably transparent to facilitate counting of the bacterial colonies and is substantially impermeable to bacteria and water vapor. As used in the specification and claims, "substantially impermeable to bacteria and moisture vapor" designates cover sheets which prevent undesired contamination of the dehydrated medium during storage and use of the devices and which will provide an environment which will support the growth of microorganisms during the incubation period. Generally, it will have the same properties as substrate 12, but need not be as stiff.

Although the illustrated embodiment of FIG. 1 includes a cover sheet 22 attached to the device, it is also contemplated within the scope of the invention that the powder-containing embodiments may be uncovered and simply placed in a sterile environment during storage and incubation. Optionally, the cover sheet 22 further may comprise a layer of adhesive (not shown) and powder (not shown). The adhesive and powder adhered to the cover sheet can have similar (or identical) properties and/or composition as the adhesive 14 and powder 16 described above and can be applied to the cover sheet in the same manner as adhesive 14 and powder 16 are applied to the substrate 12.

In another aspect, the present disclosure provides a kit. The kit can comprise any composition comprising the dried, agglomerated nutrient medium described herein. In any embodiment, the kit may include instructions for using the dried, agglomerated nutrient medium. In any embodiment, the kit may further comprise an article for obtaining a sample, processing a sample, and/or for culturing a microorganism. The article can be selected from the group consisting of a bag, a bottle, a sample acquisition device (e.g., a pipette, a swab, a sponge), and a combination of any two or more of the foregoing articles. In any of the above embodiments, the kit further may comprise a selective agent (e.g., an antibiotic). In any embodiment, the selective agent can be provided in a solution or in a substantially dry form. In any embodiment, the selective agent can be provided in a unit-dose form (e.g., a tablet, tube, or ampoule) that can be added to a predetermined volume of sample. In any embodiment, the kit further may comprise an indicator reagent used to detect a presence or an absence of a microorganism in a sample.

In any of the above embodiments, the kit may comprise a package comprising a predetermined mass of the dried agglomerated nutrient medium. In any embodiment, the predetermined mass can be an amount sufficient to be mixed with a predetermined volume (e.g., 9.9 mL, 10 mL, 90 mL, 99 mL, 100 mL, 225 mL, 1.0 L, or 3.375 L) of aqueous diluent to produce a reconstituted medium capable of facilitating the growth of a microorganism.

Certain embodiments of the methods, compositions, articles, and kits of the present disclosure are set forth in the following list of embodiments.

EMBODIMENTS

Embodiment A is a method of making a flowable, dried agglomerated nutrient medium, the method comprising:
introducing a nutrient component comprising a powdered nutrient, and an agglomeration liquid, into an agglomerator comprising a flow-through-type agglomeration chamber;
wherein the nutrient component facilitates the growth of a microorganism;
wherein the agglomeration liquid is introduced as an atomized spray;
wet-massing the nutrient component with the agglomeration liquid in the agglomeration chamber for a predetermined period of time to form agglomerated nutrient medium particles; and
exposing the agglomerated nutrient medium particles to drying conditions for a period of time to form the dried, agglomerated nutrient medium.

Embodiment B is the method of Embodiment A, wherein the agglomeration liquid consists of water.

Embodiment C is the method of Embodiment A, wherein the agglomeration liquid comprises a solvent having a dissolved nutrient that facilitates the growth of a microorganism.

Embodiment D is the method of Embodiment C, wherein the solvent comprises water, wherein the nutrient comprises peptone, sodium chloride, and sodium phosphate or potassium phosphate.

Embodiment E is the method of any one of the preceding Embodiments, wherein introducing a nutrient component comprises introducing a substantially uniform mixture of two or more powdered nutrients.

Embodiment F is the method of any one of the preceding Embodiments:

wherein introducing a nutrient component into the agglomeration chamber comprises introducing the nutrient component at a feed rate of about 50 kg/hour to about 1000 kg/hour;

wherein introducing a agglomeration liquid into the agglomeration chamber comprises introducing the agglomeration liquid at a spray rate of about 15 kg/hour to about 300 kg/hour;

wherein the agglomerator further comprises a mixing blade, wherein the mixing blade is rotated at a blade rotation rate of about 500 rpm to about 4000 rpm;

wherein exposing the agglomerated nutrient medium to drying conditions comprises exposing the agglomerated nutrient medium to a predetermined temperature of about 60° C. to about 85° C.;

wherein the feed rate, the spray rate, the blade rotation rate, and the predetermined temperature are selected to produce a dried agglomerated nutrient medium having a preselected mean water content of less than 5 weight percent.

Embodiment G is the method of any one of the preceding Embodiments:

wherein introducing a nutrient component into the agglomeration chamber comprises introducing the nutrient component at a feed rate of about 50 kg/hour to about 1000 kg/hour;

wherein introducing a agglomeration liquid into the agglomeration chamber comprises introducing the agglomeration liquid at a spray rate of about 15 kg/hour to about 300 kg/hour;

wherein the agglomerator further comprises a mixing blade, wherein the mixing blade is rotated at a blade rotation rate of about 500 rpm to about 4000 rpm;

wherein exposing the agglomerated nutrient medium to drying conditions comprises exposing the agglomerated nutrient medium to a predetermined temperature of about 60° C. to about 85° C.;

wherein the feed rate, the spray rate, the blade rotation rate, and the predetermined temperature are selected to produce a dried agglomerated nutrient medium having a gravity-packed density of 0.2 to 0.5 grams per cubic centimeter.

Embodiment H is the method of any one of the preceding Embodiments:

wherein introducing a nutrient component into the agglomeration chamber comprises introducing the nutrient component at a feed rate of about 50 kg/hour to about 1000 kg/hour;

wherein introducing a agglomeration liquid into the agglomeration chamber comprises introducing the agglomeration liquid at a spray rate of about 15 kg/hour to about 300 kg/hour;

wherein the agglomerator further comprises a mixing blade, wherein the mixing blade is rotated at a blade rotation rate of about 500 rpm to about 4000 rpm;

wherein exposing the agglomerated nutrient medium to drying conditions comprises exposing the agglomerated nutrient medium to a predetermined temperature of about 60° C. to about 85° C.;

wherein the feed rate, the spray rate, the blade rotation rate, and the predetermined temperature are selected to produce a dried agglomerated nutrient medium having particles of a first particle size distribution range of about 105 microns to about 2000 microns.

Embodiment I is the method of any one of the preceding Embodiments, further comprising selecting a subpopulation of the particles, the subpopulation having a second particle size distribution range that is narrower than the first particle size distribution range, the second particle size distribution range being about 149 microns to about 1000 microns.

Embodiment J is the method of any one of the preceding Embodiments, wherein one or more powdered nutrient is selected from the group consisting of a protein, a carbohydrate, a salt and a mixture of any two or more of the foregoing powdered nutrients.

Embodiment K is the method of any one of the preceding Embodiments, further comprising the step of subjecting the dried agglomerated nutrient medium to a process that reduces the number of viable microorganisms in the dried agglomerated nutrient medium.

Embodiment L is the method of Embodiment K, wherein subjecting the dried agglomerated nutrient medium to a process that reduces the number of viable microorganisms comprises exposing the dried agglomerated nutrient medium to ionizing radiation or to ethylene oxide vapor.

Embodiment M is a composition comprising the flowable, dried agglomerated nutrient medium produced by the method of any one of the preceding Embodiments.

Embodiment N is the composition of Embodiment M, wherein a specified mass of the dried agglomerated nutrient medium dissolves more rapidly than an equal mass of the nutrient component from which the agglomerated nutrient medium was made.

Embodiment O is a kit comprising the composition of Embodiment M or Embodiment N.

Embodiment P is the kit of Embodiment O, wherein the composition is disposed in a package comprising a predetermined mass of the dried agglomerated nutrient medium, wherein the predetermined mass is selected to be mixed with 9.9 mL, 10 mL, 90 mL, 99 mL, 100 mL, 225 mL, 1.0 L, or 3.375 L of aqueous diluent to produce a reconstituted medium capable of facilitating the growth of a microorganism.

Embodiment Q is the kit of Embodiment O or Embodiment P, further comprising an article selected from the group consisting of a bag, a bottle, and a sample acquisition device.

Embodiment R is the kit of any one of Embodiments O through Q, further comprising a selective agent and/or an indicator reagent.

Embodiment S is a thin film culture device, comprising:

a self-supporting waterproof substrate having first and second major surfaces;

an adhesive layer disposed on at least a portion of the first major surface;

a coating comprising the composition of Embodiment M or Embodiment N disposed on a least a portion of the adhesive layer; and a dry, cold-water soluble gelling agent positioned for fluidic contact with the nutrient medium.

Embodiment T is the thin film culture device of Embodiment S, further comprising a cover sheet coupled to a least a portion of the substrate, the cover sheet having a first side facing the first major surface.

Embodiment U is the thin film culture device of Embodiment T, wherein the gelling agent is adhered to the first side of the cover sheet.

Objects and advantages of this invention are further illustrated by the following examples, but the particular materials and amounts thereof recited in these examples, as well as other conditions and details, should not be construed to unduly limit this invention.

EXAMPLES

Example 1. Production of Agglomerated Nutrient Medium Particles Using a Schugi Agglomeration Process A vertical Schugi FLEXOMIX FXD-100 mixer/agglomerator (Bepex International LLC, Minneapolis, Minn.) is used for wet agglomeration. 25 kilograms of dehydrated Buffered Peptone Water ("BPW", ISO formulation, catalog number BPW010), obtained from 3M Company (St. Paul Minn.), is fed continuously via a powder dispenser at a feed rate of 300 kg/hr. The mixer/agglomerator is also fed continuously (via an array of 4 atomization nozzles) with deionized water at a feed rate of 15 L/hr. The rotating knife blade is set to a speed of 4000 rpm. The moist granulated powder at the outlet of the mixer-granulator falls continuously under gravity into a fluidized bed dryer-matched with 3 compartments. Only the first zone is used to dry the wet-agglomerated product using air heated to 60-65° C. The product is kept dry until the exhaust air reaches about 45° C. The dried, agglomerated product is sieved to collect the powder between 20-140 mesh with a major portion (e.g., more than 40%) having an affective diameter between 40-60 mesh (i.e., about 250 microns to about 400 microns). The free-flow agglomerated BPW particles obtained using this process have characteristic properties that include a gravity-packed density around 0.3-0.5 g/cm$^3$ and a dissolution time of less than 5 minutes in deionized water. The moisture content of agglomerated BPW particles is less than 5%.

Example 2-4. Production of Agglomerated Nutrient Medium Particles Using a Schugi Agglomeration Process For Examples 2-4, the same procedure as described in Example 1 is followed with the exception that the operational conditions and instrument settings (i.e. powder feed rate, liquid feed rate, blade rotating speed, drying temperature) are adjusted to the values shown in Table 1.

TABLE 1

Agglomeration parameters for Examples 1-4.

| Example No. | Powder feed rate (kg/hr) | Liquid feed rate (liter/hour) | Blade rotating speed (rpm) | Drying temperature (° C.) |
|---|---|---|---|---|
| 1 | 300 | 15 | 4000 | 60-65 |
| 2 | 300 | 22 | 4000 | 60-65 |
| 3 | 300 | 30 | 4000 | 60-65 |
| 4 | 300 | 15 | 3000 | 60-65 |

Example 5-7. Production of Agglomerated Nutrient Medium Particles Using a Schugi Agglomeration Process A vertical Schugi FLEXOMIX FX-100 with N13 nozzle combo/Fluid bed FB-5 (Bepex International LLC, Minneapolis, Minn.) is used for wet agglomeration. 25 kilograms of dehydrated Buffered Peptone Water ("BPW", ISO formulation, catalog number BPW010), obtained from 3M Company (St. Paul Minn.), is fed continuously via a powder dispenser at a feed rate of 136 kg/hr. The FX100/FB5 is also fed continuously (via an array of 4 atomization nozzles) with deionized water at a feed rate of 11.3 L/hr (example 5), 12.9 L hr (example 6), and 8.3 L/hr of 10% (w/w) of BPW solution (Example 7). The rotating knife blade is set to a speed of 4000 rpm. The moist granulated powder at the outlet of the mixer-granulator falls continuously under gravity into a fluidized bed dryer-matched with 3 compartments. Only the first zone is used to dry the wet-agglomerated product using air heated to below 80° C. The product is kept dry until the exhaust air reaches about 45° C. Table 2 shows the running conditions for each example and Table 3 shows the particle analysis resulted from the process.

TABLE 2

Agglomeration parameters for Examples 5-7.

| Example No. | Feeding liquid | Powder feed rate (kg/hr) | Liquid feed rate (liter/hour) | Blade rotating speed (rpm) | % Liquid addition |
|---|---|---|---|---|---|
| 5 | Water | 136 | 11.3 | 4000 | 7.7 |
| 6 | Water | 136 | 12.9 | 4000 | 8.6 |
| 7 | 10% BPW | 136 | 8.3 | 4000 | 5.7 |

TABLE 3

Analytical results for final product for Examples 5-7.

| Example No. | Moisture | (%) | Loss Bulk density (g/cm$^3$) | % Plus Mesh Size | | | | | | |
|---|---|---|---|---|---|---|---|---|---|---|
| | | | | 40 | 60 | 80 | 100 | 140 | 200 | 400 |
| 5 | Water | 136 | 1.0 | 7.7 | 15.9 | 23.9 | 49.5 | 73.2 | 92.5 | |
| 6 | Water | 136 | 31.5 | 57.1 | 74.2 | 81.5 | 89.9 | 95.5 | 98.9 | |
| 7 | 10% BPW | 136 | 12.4 | 29.4 | 44.7 | 51.9 | 72.4 | 86.1 | 96.8 | |

The complete disclosure of all patents, patent applications, and publications, and electronically available material cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

Various modifications may be made without departing from the spirit and scope of the invention. These and other embodiments are within the scope of the following claims.

What is claimed is:

1. A method of making a flowable, dried agglomerated nutrient medium, the method comprising:

introducing a nutrient component comprising a powdered nutrient, and an agglomeration liquid, into an agglomerator comprising a flow-through-type agglomeration chamber and a mixing blade;

wherein the nutrient component facilitates the growth of a microorganism;

wherein the agglomeration liquid is introduced as an atomized spray;

wherein introducing the nutrient component into the agglomeration chamber comprises introducing the nutrient component at a feed rate of about 50 kg/hour to about 1000 kg/hour;

wherein introducing the agglomeration liquid into the agglomeration chamber comprises introducing the agglomeration liquid at a spray rate about 15 kg/hour to about 300 kg/hour;

wet-massing the nutrient component with the agglomeration liquid in the agglomeration chamber for a predetermined period of time to form agglomerated nutrient medium particles;

exposing the agglomerated nutrient medium particles to drying conditions for a period of time to form the dried, agglomerated nutrient medium;

wherein the mixing blade is rotated at a blade rotation rate of about 500 rpm to about 4000 rpm;

wherein exposing the agglomerated nutrient medium to drying conditions comprises exposing the agglomerated nutrient medium to a predetermined temperature about 60° C. to about 85° C.;

wherein the feed rate, the spray rate, the blade rotation rate, and the predetermined temperature are selected to produce a dried agglomerated nutrient medium having particles of a first particle size distribution range of about 105 microns to about 2000 microns; and isolating a subpopulation of the particles, the subpopulation having a second particle size distribution range that is narrower than the first particle size distribution range, the second particle size distribution range being about 149 microns to 1000 microns.

2. The method of claim 1, wherein the agglomeration liquid consists of water.

3. The method of claim 1, wherein the agglomeration liquid comprises a solvent having a dissolved nutrient that facilitates the growth of a microorganism.

4. The method of claim 1, wherein introducing a nutrient component comprises introducing a substantially uniform mixture of two or more powdered nutrients.

5. The method of claim 1:

wherein introducing a nutrient component into the agglomeration chamber comprises introducing the nutrient component at a feed rate of about 50 kg/hour to about 1000 kg/hour;

wherein introducing an agglomeration liquid into the agglomeration chamber comprises introducing the agglomeration liquid at a spray rate of about 15 kg/hour to about 300 kg/hour;

wherein the agglomerator further comprises a mixing blade, wherein the mixing blade is rotated at a blade rotation rate of about 500 rpm to about 4000 rpm;

wherein exposing the agglomerated nutrient medium to drying conditions comprises exposing the agglomerated nutrient medium to a predetermined temperature of about 60° C. to about 85° C.;

wherein the feed rate, the spray rate, the blade rotation rate, and the predetermined temperature are selected to produce a dried agglomerated nutrient medium having a preselected mean water content of less than 5 weight percent.

6. The method of claim 1:

wherein introducing a nutrient component into the agglomeration chamber comprises introducing the nutrient component at a feed rate of about 50 kg/hour to about 1000 kg/hour;

wherein introducing an agglomeration liquid into the agglomeration chamber comprises introducing the agglomeration liquid at a spray rate about 15 kg/hour to about 300 kg/hour;

wherein the agglomerator further comprises a mixing blade, wherein the mixing blade is rotated at a blade rotation rate of about 500 rpm to about 4000 rpm;

wherein exposing the agglomerated nutrient medium to drying conditions comprises exposing the agglomerated nutrient medium to a predetermined temperature about 60° C. to about 85° C.;

wherein the feed rate, the spray rate, the blade rotation rate, and the predetermined temperature are selected to produce a dried agglomerated nutrient medium having a gravity-packed density of 0.2 to 0.5 grams per cubic centimeter.

7. The method of claim 1, wherein one or more powdered nutrient is selected from the group consisting of a protein, a carbohydrate, a salt and a mixture of any two or more of the foregoing powdered nutrients.

8. The method of claim 1, further comprising the step of subjecting the dried agglomerated nutrient medium to a process that reduces the number of viable microorganisms in the dried agglomerated nutrient medium.

9. The method of claim 8, wherein subjecting the dried agglomerated nutrient medium to a process that reduces the number of viable microorganisms comprises exposing the dried agglomerated nutrient medium to ionizing radiation or to ethylene oxide vapor.

* * * * *